US010687901B2

(12) United States Patent
Thomas

(10) Patent No.: US 10,687,901 B2
(45) Date of Patent: Jun. 23, 2020

(54) METHODS AND SYSTEMS FOR REGISTRATION OF VIRTUAL SPACE WITH REAL SPACE IN AN AUGMENTED REALITY SYSTEM

(71) Applicant: Monroe Milas Thomas, Toronto (CA)

(72) Inventor: Monroe Milas Thomas, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 1 day.

(21) Appl. No.: 15/531,483

(22) PCT Filed: Aug. 17, 2016

(86) PCT No.: PCT/CA2016/050961
§ 371 (c)(1),
(2) Date: May 30, 2017

(87) PCT Pub. No.: WO2018/032083
PCT Pub. Date: Feb. 22, 2018

(65) Prior Publication Data
US 2018/0303558 A1 Oct. 25, 2018

(51) Int. Cl.
*A61B 34/20* (2016.01)
*G06T 7/50* (2017.01)
(Continued)

(52) U.S. Cl.
CPC ............. *A61B 34/20* (2016.02); *A61B 34/10* (2016.02); *A61B 34/30* (2016.02); *A61B 90/36* (2016.02);
(Continued)

(58) Field of Classification Search
CPC ............ A61B 34/20; A61B 2034/2055; A61B 2034/2065; G06F 3/017; G06T 19/20; G06T 7/70; G06T 19/006; G06T 7/50
See application file for complete search history.

(56) References Cited

U.S. PATENT DOCUMENTS

| | | | |
|---|---|---|---|
| 6,298,262 B1 | 10/2001 | Franck et al. | |
| 6,336,082 B1* | 1/2002 | Nguyen | G06K 9/6255 340/658 |
| 6,609,022 B2 | 8/2003 | Vilsmeier et al. | |
| 2005/0215879 A1* | 9/2005 | Chuanggui | G06T 7/001 600/407 |

(Continued)

FOREIGN PATENT DOCUMENTS

WO 2014043661 A2 3/2014

OTHER PUBLICATIONS

"Coordinate systems", online: Microsoft, Inc. <https://developer.microsoft.com/en-us/windows/mixed-reality/coordinate_systems>.
(Continued)

*Primary Examiner* — Samantha (Yuehan) Wang
(74) *Attorney, Agent, or Firm* — Rowand LLP

(57) ABSTRACT

A method and system to use an augmented reality device in a surgical procedure. The method includes rendering, on the display of the device, a model of a patient reference object; in response to receiving input, moving the model of the patient reference object in an augmented reality coordinate system; determining that the model is aligned with the patient reference object in real world space when viewed through the display and, based on that determination, identifying a first transform from the augmented reality coordinate system to a navigation coordinate system used by an optical navigation system for tracking the patient reference object; subsequently transferring patient image data from the navigation coordinate system to the augmented reality coordinate system using an inverse of the first transform; and displaying the patient image data on the display to augment a real world view of a patient.

21 Claims, 10 Drawing Sheets

(51) Int. Cl.
*A61B 34/10* (2016.01)
*A61B 90/00* (2016.01)
*A61B 34/30* (2016.01)
*G06T 7/70* (2017.01)
*G06F 3/01* (2006.01)
*G06T 19/00* (2011.01)
*G06T 19/20* (2011.01)
*A61B 90/50* (2016.01)
*G16H 20/40* (2018.01)

(52) U.S. Cl.
CPC .............. *A61B 90/39* (2016.02); *G06F 3/017* (2013.01); *G06T 7/50* (2017.01); *G06T 7/70* (2017.01); *G06T 19/006* (2013.01); *G06T 19/20* (2013.01); *A61B 90/361* (2016.02); *A61B 2034/2048* (2016.02); *A61B 2034/2055* (2016.02); *A61B 2034/2065* (2016.02); *A61B 2090/365* (2016.02); *A61B 2090/3975* (2016.02); *A61B 2090/502* (2016.02); *G16H 20/40* (2018.01)

(56) References Cited

U.S. PATENT DOCUMENTS

2014/0282008 A1 9/2014 Verard et al.
2016/0191887 A1* 6/2016 Casas .................. H04N 13/239
 348/47
2017/0367766 A1* 12/2017 Mahfouz ................ A61B 34/10

OTHER PUBLICATIONS

"3D Medical Interpretation", online: Microsoft Studios <https://microsoftstudios.com/hololens/shareyouridea/idea/3d-medical-interpretation/>.
International Search Report from PCT/CA2016/050961 dated Apr. 24, 2017.
Written Opinion from PCT/CA2015/050961 dated Apr. 24, 2017.
CA Application No. 2 892 554 filed Mar. 14, 2014.
CA Application No. 2 896 381 filed Mar. 14, 2014.
CA Application No. 2 929 702 filed Mar. 14, 2014.
CA Application No. 2 948 719 filed Mar. 14, 2014.

* cited by examiner

METHODS AND SYSTEMS FOR REGISTRATION OF VIRTUAL SPACE WITH REAL SPACE IN AN AUGMENTED REALITY SYSTEM

FIELD

The present application generally relates to augmented reality systems and, in particular, methods and systems for registering a virtual space with a real world space using an augmented reality system.

BACKGROUND

Augmented reality (AR) systems and virtual reality systems are undergoing rapid development. An augmented reality system typically involves a headset or glasses that allow a wearer to observer the real world, but supplement that view with additional rendered images on the lenses of the headset or glasses. As an example Google Glass™ augmented reality glasses may be used to display data and other effects to a user while still viewing the real world. Virtual reality systems tend to be more immersive so that the wearer sees only the rendered virtual reality world on a wide field of view headset. A recently-developed AR device from Microsoft is branded HoloLens™. The HoloLens™ headset uses a plurality of cameras and sensors to try to build upon knowledge of the location and orientation of the headset in a real world space while rendering a "hologram" object that appears to the wearer as though it is in the real world space. The "hologram" is a stereoscopic rendering of a computer-modelled object.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimens, and radiation therapy are only a few examples of procedures utilizing imaging guidance in the medical field. Optical tracking systems, used during a medical procedure, track the position of a part of the instrument that is within line-of-site of the optical tracking camera. These optical tracking systems also require a reference to the patient to know where the instrument is relative to the target (e.g., a tumour) of the medical procedure.

Pre-operative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the pre-operative scans, allowing for instruments to be viewed on a monitor in the context of the pre-operative information.

Augmented reality systems may have a role to play in future surgical procedures.

BRIEF SUMMARY

The present application describes a method of using an augmented reality device in a surgical procedure that uses an optical navigation system that optically tracks a patient reference object to locate the patient reference object in a real world space and determine its coordinates in a navigation coordinate system, wherein the augmented reality device has a display through which a wearer views the real world space and on which the augmented reality device may render modeled objects, wherein the augmented reality device includes sensors for determining a position and orientation of the augmented reality device in the real world space using an augmented reality coordinate system. The method includes rendering, on the display, a model of the patient reference object; in response to receiving input, moving the model of the patient reference object in the augmented reality coordinate system; determining that the model is aligned with the patient reference object in the real world space when viewed through the display and, based on that determination, identifying a first transform from the augmented reality coordinate system to the navigation coordinate system; subsequently transferring patient image data from the navigation coordinate system to the augmented reality coordinate system using an inverse of the first transform; and displaying the patient image data on the display to augment a real world view of a patient.

In another aspect, the present application describes a surgical navigation system to track objects during a surgical procedure. The surgical navigation system includes an optical tracking system that optically tracks a patient reference object to locate the patient reference object in a real world space and determine its coordinates in a navigation coordinate system; and an augmented reality device having a display through which a wearer views the real world space and on which the augmented reality device may render modeled objects, and including sensors for determining a position and orientation of the augmented reality device in the real world space using an augmented reality coordinate system, the augmented reality device to render a model of the patient reference objection on the display and to receive input moving the model of the patient reference object in the augmented reality coordinate system. The augmented reality device is to determine that the model is aligned with the patient reference object in the real world space when viewed through the display. The optical tracking system or the augmented reality device is to, based on the determination of alignment, identify a first transform from the augmented reality coordinate system to the navigation coordinate system, and to subsequently transfer patient image data from the navigation coordinate system to the augmented reality coordinate system using an inverse of the first transform. The augmented reality system is to display the patient image data on the display to augment a real world view of a patient.

It will be appreciated that the augmented reality system contains a number of sensors for determining its position and orientation in the real world, including sensors for determining the "gaze" of the wearer. That is, the augmented reality system may include sensors for tracking a wearer's retina so as to determine the user's gaze or focus, i.e. angle of view, which may be used by the augmented reality system in determining the mapping from the real world space to an augmented reality space so as to account for parallax effects. These implementation details of augmented reality systems will be appreciated by those ordinarily skilled in the art of augmented reality and are not further detailed herein. References herein to sensors for the determination of the system's position and/or orientation in the real world may be understood to also include sensors for determining gaze or focus of the wearer's eyes in some embodiments.

In yet a further aspect, the present application describes non-transitory computer-readable media storing computer-executable program instructions which, when executed, configured a processor to perform the described methods.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

The phrase "registration" or "image registration" refers to the process of determining the transform to be used in correlating three-dimensional points across different coordinate systems. Registration links two different coordinate systems to that data positioned in one coordinate system may be mapped to the other coordinate system using the transform. Data may include photographs, data from different sensors, times, depths, or viewpoints. The process of "registration" is used in some of the described examples for medical imaging in which images from different imaging modalities are co-registered. Registration is used in order to be able to compare or integrate the data obtained from these different modalities for presentation on a common platform or display.

When it comes to registration of imaging data with optical tracking data, those skilled in the relevant arts will appreciate that there are numerous registration techniques available and one or more of the techniques may be applied in implementations of the present application. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 1:
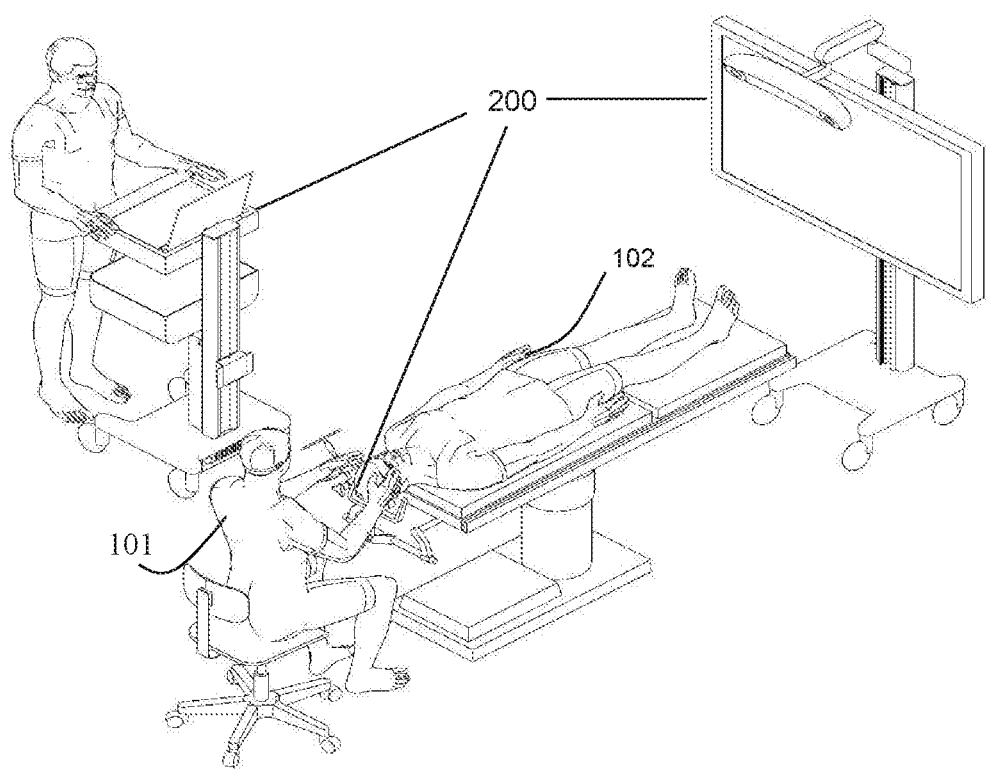
FIG. 1 diagrammatically illustrates, in perspective view, a navigation system.

Reference is first made to FIG. 1, which diagrammatically illustrates, in perspective view, a navigation system 200, such as a medical navigation system. The navigation system 200 is positioned in an operating room (OR) to be used to guide a surgeon in conducting a surgical procedure. In this example, the navigation system 200 supports, facilitates, and enhances minimally-invasive access port based surgery using a minimally-invasive access port-based surgical procedure. In this example, a surgeon 101 conducts a minimally-invasive access port based surgery on a subject, such as a patient 102, in an OR environment. The surgery may be a neurosurgery, as in this example. In these circumstances, the surgeon 101 is positioned proximate the head of the patient 102.

In addition to the navigation system 200, the operating room may contain other equipment, such as surgical tool trays, carts, and booms. Some of this equipment may feature surgical lights, oxygen or other gas supplies, anesthesia supplies, etc., depending on the nature of the surgery being performed.

Figure 2:
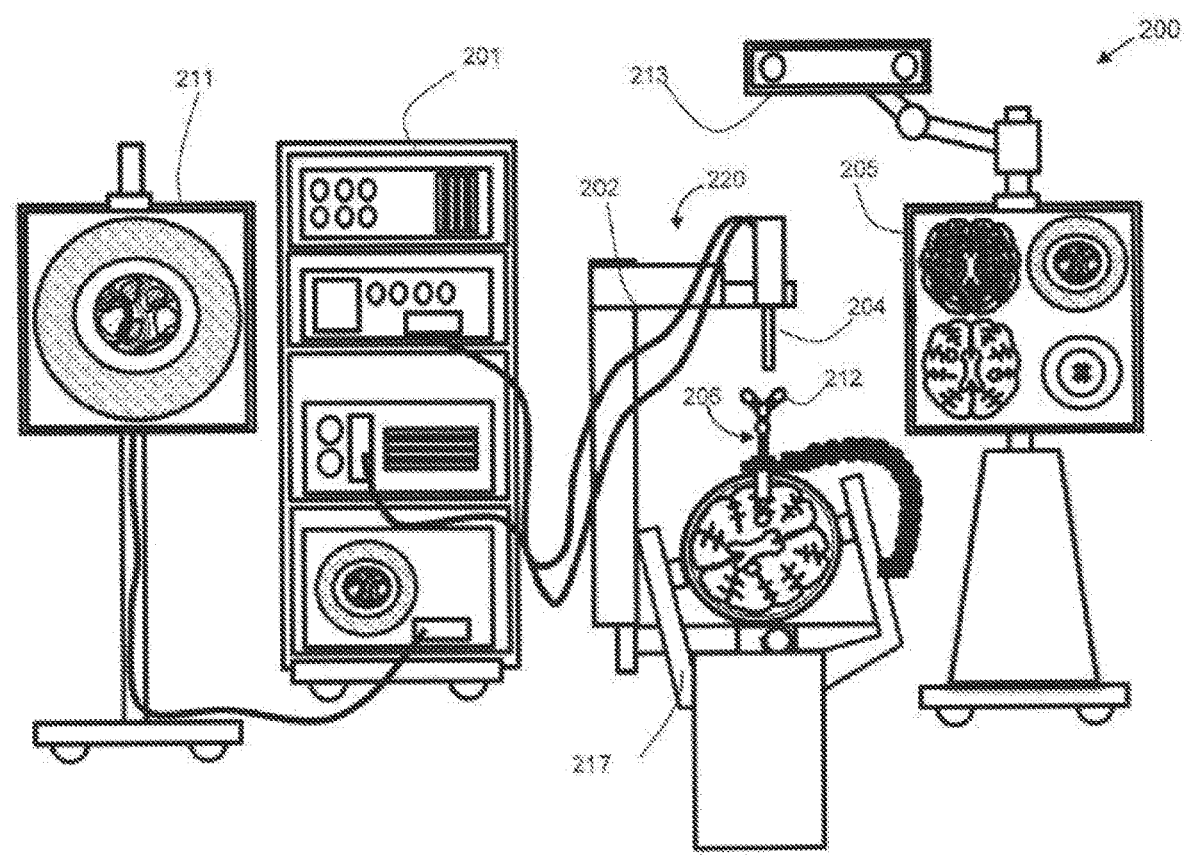
FIG. 2 diagrammatically illustrates an example of the navigation system.

Reference is now made to FIG. 2, which diagrammatically illustrates an example of the navigation system 200. The navigation system 200 may include an equipment tower 201, a tracking system 213, and at least one display device. e.g., a primary display device 211 and a secondary display device 205. The tracking system 213 may include optical imaging devices, e.g. cameras. In this example, the tracking system 213 includes two laterally spaced-apart cameras for stereoscopic vision. The camera may be a three-dimensional (3D) optical tracking stereo camera, such as a Northern Digital Imaging® (NDI) optical tracking stereo camera, by way of example. The navigation system 200 is to track at least one instrument, such as a surgical instrument, e.g., an access port 206, for assisting the surgeon 101 during the minimally-invasive access port-based surgical procedure.

The navigation system 200 may further include a device positioning unit, also referred to as a drive unit 220, having a robotic arm 202 that supports an optical device, such as an optical scope 204 or camera. The optical scope 204 may be positioned in line with the trajectory of access (co-axial with the access port 206) to enable the surgeon 101 (FIG. 1) to view down the access port 206. In the case where the optical scope 204 includes an image sensor, like a camera, the view may be displayed on one of the displays 205, 211 to assist the surgeon 101 in navigation. The view may also be integrated with other data, including pre-surgical plan information, pre-surgical imaging (like MRI, CAT scan, or ultrasound imaging, for example), and may be registered on the basis of registration of the patient in the OR space and registration of the surgical equipment relative to the patient, as tracked by the navigation system 200. The navigation system 200 may also track surgical instruments, like the access port 206 or other tools, in the OR space and may map models of those tools to a virtual space to which patient data has been mapped in order to render a combined display of the tools and the patient and/or pre-surgical imaging on the displays 205, 211.

The equipment tower 201 may be mountable on a frame, e.g., a rack or a cart, and is configured to accommodate at least one of a computer operable by at least one a set of instructions, storable in relation to at least one non-transitory memory device, corresponding to at least one of planning software, navigation software, and robotic software, and a power supply, e.g., an AC adapter power supply.

In some example surgeries, a patient's head may be retained by a head holder 217, a craniotomy is performed, a dura flap is formed and retracted, and the access port 206 is inserted into the patient's brain. The tracking system 213 tracks and determines, e.g., in real-time by way of a set of instructions corresponding to tracking software and storable in relation to at least one non-transitory memory device, location data of at least one OR item, such as the robotic arm 202 and the at least one instrument, e.g., the access port 206. The tracked instrument may include at least one fiducial marker 212 mounted in fixed relation to the at least one OR item, e.g., the robotic arm 202 and the at least one instrument, e.g., the access port 206.

The secondary display device 205 may be configured to display real-time output from the navigation system 200. The displayed data may include at least one of an axial view, a sagittal view, at least one coronal view, and a view oriented relative to the at least one instrument, such as perpendicular to a tool tip, in-plane of a tool shaft, etc. The display may include multiple views.

The fiducial marker 212 may be a reflective sphere where the tracking system 213 is an optical tracking device. In some embodiments, the tracking system 213 may detect electromagnetic emissions and the fiducial marker 212 may be an electromagnetic marker. The three-dimensional position of the at least one fiducial marker 212 is determined by the tracking system 213 which is then able to map the location of the fiducial marker 212 to a virtual coordinate space and, thereby, position a model of the instrument to which the fiducial marker 212 is attached in the virtual coordinate space. The marker positions could be tracked relative to an object in the operating room such as the patient. Other types of markers that could be used would be RF, EM, LED (pulsed and un-pulsed), glass spheres, reflective stickers, or unique structures and patterns. The RF and EM may have specific signatures for the specific tools to which they are attached. The reflective stickers, structures, and patterns, glass spheres, LEDs may be detected using optical detectors, while RF and EM may be detected by using antennas.

Figure 3:
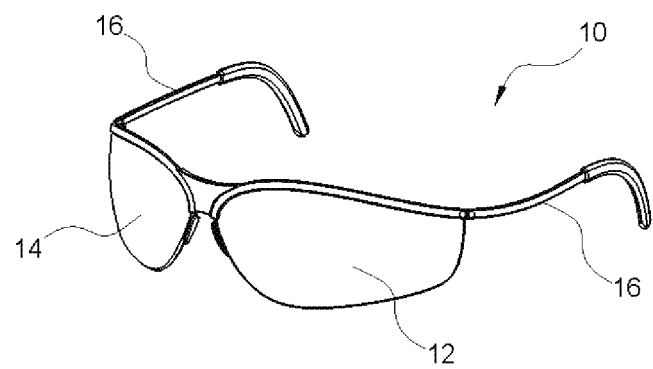
FIG. 3 shows a perspective view of an example augmented reality device.

FIG. 3 shows an example embodiment of an augmented reality (AR) device 10. AR devices generally include a transparent or nearly transparent display screen configured to be in front of a user's eyes so that the user is able to view the real world through the display screen, and the devices are capable of rendering objects on the display screen to augment the user's view of the real world. In this example, the augmented reality device 10 is configured as a pair of glasses with a left lens or display 12 and a right lens or display 14, and a pair of arms 16 to fit over the top and back of a user's ears to hold the augmented reality device 10 in place. Other configurations and designs may be used in other embodiments, include headsets, headstraps, faceplates, or other features to hold one or more transparent displays in front of a user's field of view and to move with the user's head. In this example, the augmented reality device 10 includes the left display 12 and the right display 14, which the augmented reality device 10 may manipulate individually in order to render images stereoscopically, giving the impression of depth to objects rendered on the displays 12, 14.

Figure 4:
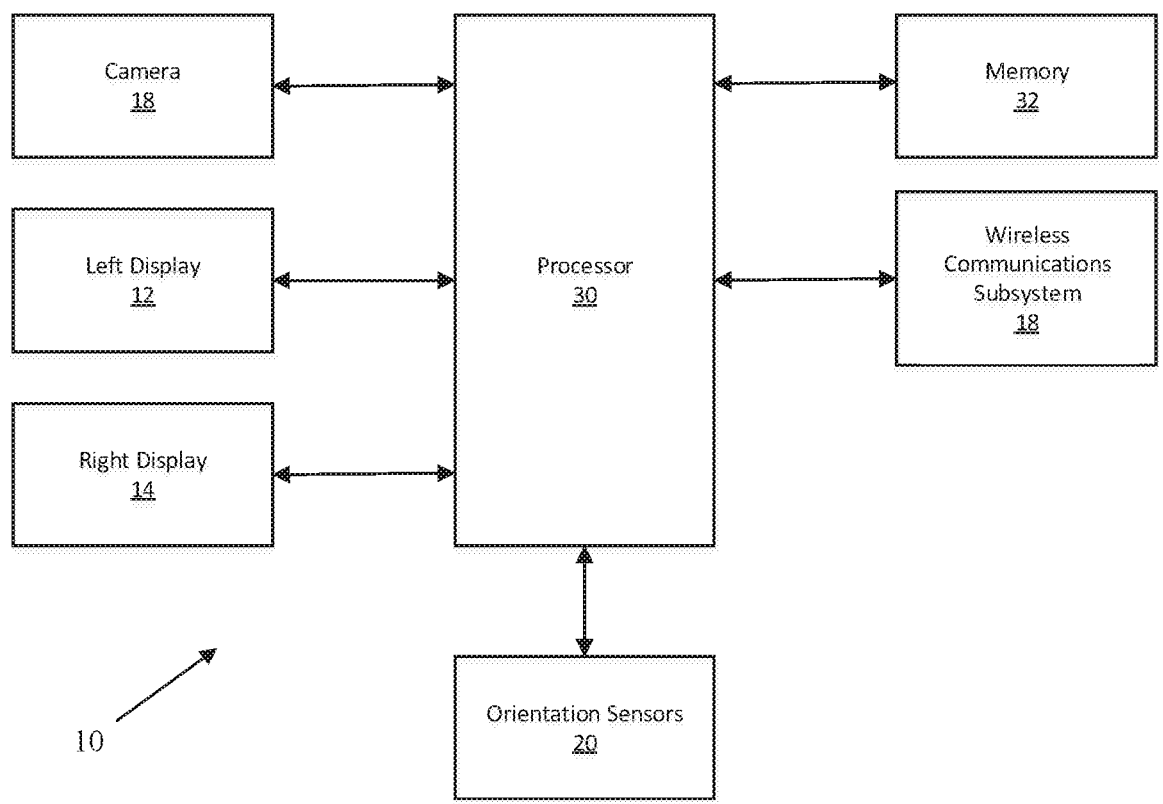
FIG. 4 shows, in block diagram for, an example augmented reality device.

Reference is now made to FIG. 4, which shows, in block diagram form, an example embodiment of the augmented reality device 10. The augmented reality device 10 include a processor 30, a memory 32 and a display, which in this example is formed from the left display 12 and the right display 14. The displays 12, 14 are, integrated within transparent or semi-transparent lenses or visors through which a user may view the real world. Objects rendered on the displays 12, 14 are thus rendered within the user's line-of-sight of the real world.

The augmented reality device 10 further includes orientation sensors 20 for determining changes in position or orientation of the augmented reality device 10 in the real world. This enables the augmented reality device 10 to adjust its rendering of objects to reflect the changes in user line-of-sight, so as to make the objects appear as though they are positioned in the real world. The orientation sensors 20 may include, for example, accelerometers, gyroscopes, proximity sensors, etc.

The augmented reality device 10 may further include one or more cameras 18. The cameras 18 may be directed toward the user's field of view for the purpose of identifying objects in the field of view as a part of adjusting the augmented reality device's 10 mapping of the augmented reality coordinate system to the real world environment. The cameras 18 may alternatively or also be used for gesture recognition and other input functions. Processing of stereoscopic image data from the cameras 18 may be used to augment the orientation sensors 20 data to improve the accuracy of the calculated position and orientation of the wearer.

The augmented reality device 10 may also include a wireless communication subsystem 34 for communicating with remote systems and computing devices. In some cases, the wireless communication subsystem 34 may communicate with a handheld device, such as an input device, for receiving user input. Some examples include a wand for gesture input, a mobile phone, a smartwatch, a keyboard, a mouse, or the like. In some cases, the wireless communication subsystem 34 may communicate with remote computing devices, including servers and the like. In some examples below, the wireless communication subsystem 34 may communicate with computing devices in an operating room environment, such as a navigation system. Various protocols may be used in various implementations, including IEEE 802.11 (WiFi), Bluetooth™, near field communications, ZigBee™, or any other suitable protocols.

It will be appreciated that the augmented reality device 10 is generally arranged to be worn as glasses or a headset by a user. The various above-described components may be incorporated into the headset or may be partly housed in a nearby computing device connected to the headset by a wired or wireless communication link.

It will also be appreciated that various components have been omitted for ease of explanation and clarity, including batteries, charging circuitry, etc.

Figure 5:
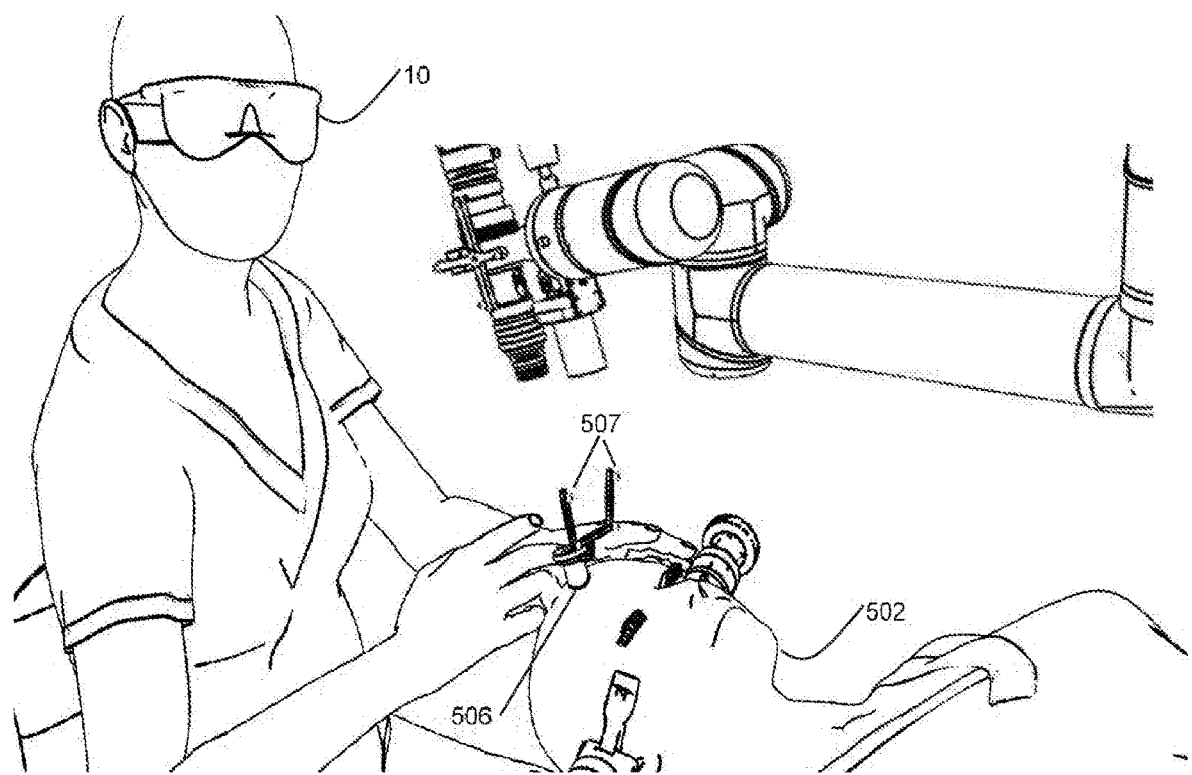
FIG. 5 shows a view of an example access port-based surgical procedure being conducted using an augmented reality device.

FIG. 5 shows a view of an example access port-based surgical procedure being conducted using the navigation system 200. In this example, a surgeon 501 is resecting a tumor from the brain of a patient 502 through an access port 506. In some procedures, an external scope is coupled with a robotic arm, and is used to view down access port at a sufficient magnification to allow for enhanced visibility down port. The output of external scope may be rendered on a visual display, such as a display device mounted perpendicular to the surgeon 501 for ease of viewing. The surgeon 501 in such a situation must look up from the patient to observe detail on the display while manipulating tools.

Active or passive fiduciary markers, 507, e.g., spherical markers, are disposed in a fixed geometrical arrangement in fixed relation to at least one of the access port 506 and the external scope for facilitating their tracking (location of these tools) by the tracking system. The active or passive fiduciary markers 507 are sensed by sensors of the tracking system, whereby identifiable points are provided. A tracked instrument is typically identified by a sensing a grouping of active or passive fiduciary markers 507 whereby a rigid body, such as a tool, is identified by the tracking system, and whereby the position and pose in 3D of a tracked instrument, such as a tool, is determinable. Typically, a minimum of 3 active or passive fiduciary markers 507 are placed on a tracked tool to define the instrument. In many embodiments, four active or passive fiduciary markers 507 are used to track each tool. By tracking the 3D location of the tool, the system may render the tool on the display being observed by the surgeon 501 so that the surgeon 501 is able to view the tool together with images from the scope and/or images from pre-operative scans. In this manner, the surgeon 501 is guided in manipulating the tool relative to the patient's anatomy and/or pre-operative imaging data.

In this example embodiment, the surgeon 501 may be wearing the augmented reality device 10. The augmented reality device 10 is another mechanism to provide the surgeon 501 with information to guide the surgery or improve the ability of the surgeon 501 to accurately manipulate tools by augmenting the surgeon's 501 real world view with imaging data. The imaging data provided or rendered on the display 12, 14 (FIG. 4) of the augmented reality device 10 may include pre-operative scan data, a model of the tool, patient vitals or other information, and/or pre-operative plan information. As an example, the augmented reality device 10 may overlay pre-operative scan data on the surgeon's view of the real-world patient so that the surgeon 501 is able to see a 3D rendering of, for example, CAT scan data aligned with the patient's head while looking directly at the patient. As another example, the augmented reality device 10 may render a model of the tool aligned directly with the real-world tool so that as the surgeon manipulates the tool into layers of the patient's brain and loses real-world sight of the tip of the tool, the modelled version still shows the position of the tip of the tool, which may further be supplemented by rendering on the augmented reality device 10 of a planned trajectory or other information to aid the surgeon 501 in guiding the tip of the tool. In yet another example, the augmented reality device 10 may render "dashboard" information, such as patient vitals or other monitored data, so that the surgeon 501 has that information available directly in their peripheral vision. In some examples, the dashboard information may be "head locked", i.e. the augmented reality device 10 maintains the display in the surgeon's field of view irrespective of where the surgeon 501 is looking, or "room locked", i.e. the augmented reality device 10 maintains the display in the same location in the room, as though it were a fixed real-world display screen, irrespective of where the surgeon 501 is looking. In yet a further example, the augmented reality device 10 may render pre-operative plan information, such as craniometrical cut-lines for opening access to the skull, so as to guide the surgeon 501 during the operation. From these examples and the description herein, those ordinarily skilled in the art will appreciated the range of other possible information that may be displayed by the AR device 10 in order to assist the surgeon 501 during planning, testing, practice, or actual surgical procedures.

One of the challenges in using the augmented reality device 10 in these situations is registration. The augmented reality device 10 operates by determining its position in the real world and then attempting to track its movement in the real world using various sensors so that virtual objects for which it has a three-dimensional position in its augmented reality coordinate system, are 'moved' in a way that makes them appear to the wearer as though they are in a given position in the real world. In the case of surgical procedures, an accurate registration between the imaging data being rendered and the real world is important.

In the case of surgical navigation systems, registration is also important to ensure that the system is accurately able to track the location of objects relative to a patient. That registration process, in various implementations, can be performed in relation to a base reference frame and is performable by various techniques, such as (a) identifying features (natural or engineered) on the MR and CT images and pointing to those same features in the live scene using a pointer tool that is tracked by the tracking system; (b) tracing a line on the curved profile of the patient's face or forehead with a pointer tool that is tracked by the tracking system and matching this curved profile to the 3D MR or CT volume; (c) applying a tool of known geometry to the patient's face or forehead, where the tool is trackable by the tracking system; and (d) using a surface acquisition tool based on structured light and matching an extracted surface to the 3D MR or CT volume. As an example, registration using fiducial touch-points may include first identifying fiducial touch-points on images, then touching the fiducial touch-points with a tracked instrument and determining registration data in relation to reference markers. In another example, the registration may involve conducting a surface scan procedure by scanning the face using a 3D scanner, extracting the face surface data from MR/CT data, and determining registration data points by matching the face surface data from the 3D scanner with the face surface data from MR/CT data. These techniques may be used in tandem to complete a registration. In some procedures, an initial registration may be supplemented or refined with additional registration operations during the course of a surgery.

A registration is needed between the coordinate frame of a tracking system, the physical location of the patient in space, and the coordinate frame of the corresponding image data for the patient. This registration is typically obtained relative to a tracked patient reference object or marker that can be tracked by the navigation system and which is placed in a fixed position relative to the patient anatomy of interest and thus can be used as a fixed reference for the anatomy. Generally, this can be accomplished by attaching the patient reference object to a patient immobilization frame (such as a clamp for skull fixation in neurosurgery), which itself is rigidly attached to the patient.

Figure 6:
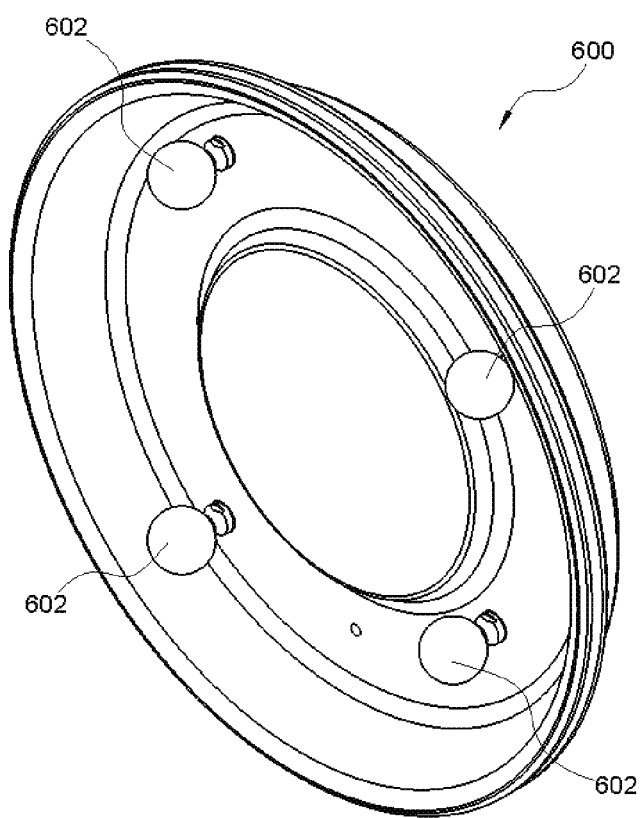
FIG. 6 shows an example of a patient reference object trackable by an optical navigation system.

One example of a patient reference object 600 is shown in FIG. 6. The patient reference object 600 includes a plurality of fiducial markers 602. In this example, the patient reference object 600 includes four fiducial markers 602, however it will be understood that other examples may include more or fewer markers. The fiducial markers 602 may include passive (e.g. IR reflective) markers, active (e.g. transmitting) markers, or both passive and active markers. The fiducial markers 602 are arranged in a non-uniform geometry so that the position and orientation of the patient reference object 600 is uniquely determinable by the navigation system based on identifying the relative location of the fiducial markers 602.

The example patient reference object 600 is only one example of a device that is trackable by the navigation system and used in the navigation system registration process. As will be clear from the discussion below, although many of the examples described below employ the patient reference object 600 in a registration process for the augmented reality device, other trackable devices may be used instead.

Figure 7:
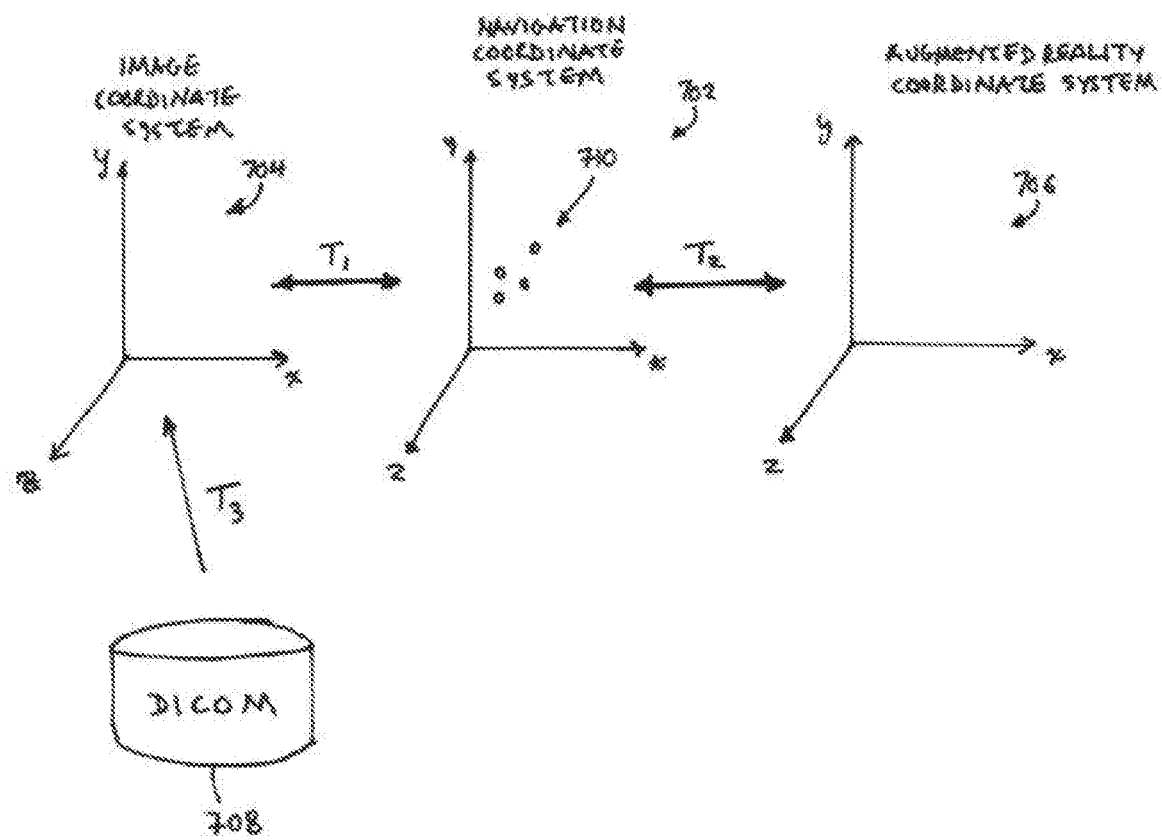
FIG. 7 diagrammatically illustrates coordinate systems.

Reference is now made to FIG. 7, which illustrates examples of the various coordinate systems and their relationships. In particular, as described above, a navigation coordinate system 702 tracks the position of objects in the real world space, including fiducial markers 710 mounted to a patient reference object 600 (FIG. 6). A registration process is used to ensure the navigation coordinate system 702 has an accurate location for the patient, and that location is then tracked by tracking the patient reference object 600.

The registration process results in determining a first transform $T_1$ between an image coordinate system 704 and the navigation coordinate system 702. This allows image data in the image coordinate system 704 to be converted to image data in the navigation coordinate system 702, which may then be rendered on a display screen together with tracked instruments and objects for which the navigation system determines a location in the real world.

The augmented reality device maintains an augmented reality coordinate system 706. In order for objects from the image coordinate system 704 and/or the navigation coordinate system 702 to be displayed on the display of the augmented reality device, a second transform $T_2$ may be used to map objects from the navigation coordinate system 702 to the augmented reality coordinate system 706. Accordingly, a registration process may be used to determine the second transform $T_2$ that relates the navigation coordinate system 702 to the augmented reality coordinate system 706. It will be appreciated that a combined transform $T_{12}$ formed from $T_1$ and $T_2$ may be used to map objects in one step from the image coordinate system 704 to the augmented reality coordinate system 706.

In will also be understood that a third transform $T_3$ may be used in loading image data from a DICOM system into the image coordinate system 704.

In accordance with one aspect of the present application, the registration process for the augmented reality device includes rendering a model of a trackable real world object on the display. The model rendered in augmented reality matches the size and shape of the corresponding real world object. The model has an initial position within the augmented reality coordinate system and is displayed at that location. The augmented reality device allows for manipulation of virtual objects, like the model, so as to change their position and orientation in response to user input. The input mechanisms may include hand movements or gestures detected by the augmented reality device or input through an input device, like a mouse, hand-held input device (e.g. a wand or the like), voice commands, or any other input mechanism suitable to the implementation. In this manner, the augmented reality system adjusts the position of the model in the augmented reality coordinate system in response to received user instructions, and the display is updated to reflect the changed position of the It will further be appreciated that the display is updated based on movement of the wearer's head. This is a function of the augmented reality device tracking its own position and movement in the real world and applying those changes in position and orientation to its own mapped location in the augmented reality coordinate system. In this manner, the device renders a view of virtual objects based on the position of those objects in the augmented reality coordinate system and the position and viewpoint of the augmented reality device itself within that coordinate system.

The navigation system tracks trackable real world objects, like the patient reference object. The corresponding virtual object is manipulated within the augmented reality coordinate system until it is brought into alignment with the real world object from the viewpoint of the wearer of the augmented reality device. Once alignment is achieved, that alignment serves as the basis for determining the relationship, and transform, between the augmented reality coordinate system and the navigation coordinate system. For example, once the virtual object is aligned with the real world object, the augmented reality device obtains coordinate data for the tracked real world object from the navigation system in terms of navigation coordinate system coordinates, and determines the applicable transform for translating that location in the navigation coordinate system to the coordinates for the corresponding and aligned virtual object in the augmented reality system. The transform thus determined then links the navigation coordinate system to the augmented reality coordinate system, and may be used to map other tracked objects, images or data from the navigation coordinate system to the augmented reality coordinate system for rendering on the augmented reality display.

In the example case of the patient reference object 600 (FIG. 6), the navigation system identifies a set of fiducial markers 710 corresponding to the patient reference object using, for example, optical tracking with an IR-sensitive stereoscopic camera (other tracking technology may be used in other embodiments). It tracks the position of those fiducial markers 710 in the navigation coordinate system 702. From this information it is able to track the location of the patient (based on the registration process that linked patient location to the patient reference object) within the navigation coordinate system 702. Image data from the image coordinate system 704 may be mapped to the navigation coordinate system 702 using the first transform $T_1$.

Figure 8:
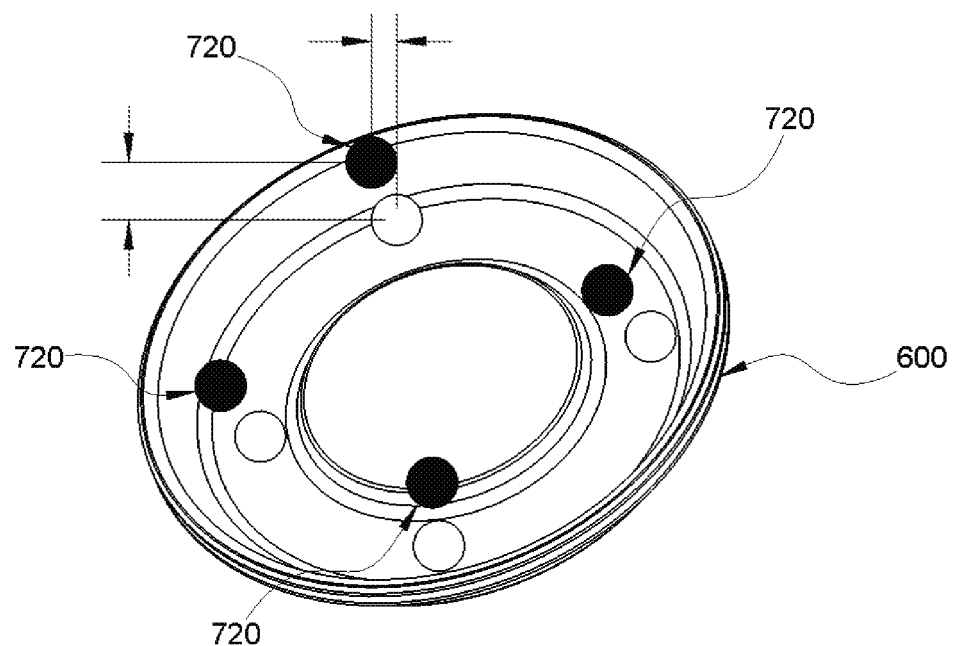
FIG. 8 shows correspondence between an example patient reference object and a model of the example patient reference object.

A wearer of the augmented reality device views the operating room, including the patient and the patient reference object. The augmented reality device augments the real world view of the operating room with virtual models rendered on the display. It tracks its own location and orientation in an augmented reality coordinate system, and the models have a location within the augmented reality coordinate system. A virtual model 712 of the patient reference object is shown on the display. A wearer then provides input to manipulate the location of that virtual model 712 of the patient reference object so as to try to align it with the real world patient reference object. Once the virtual model 712 is aligned with the real world patient reference object, the relationship between the navigation coordinate system and the augmented reality coordinate system is determined by the coordinate transforms between the locations of the fiducials 710 tracked on the patient reference object and the locations of the corresponding fiducials on the model 712 of the patient reference object in the augmented reality coordinate system. Reference is now also made to FIG. 8, which shows a perspective view of the real world patient reference object 600 and virtual fiducials 720 rendered as part of the virtual model (the remainder of the model is not shown for clarity), as viewed on the display of the augmented reality device.

In some example implementations, the manipulation of the virtual object to align it with the real world object may be partly or wholly automated by the augmented reality device based on image recognition. For example, the user may be prompted to generally align the virtual object with the real world patient reference object. This initial alignment may be termed a "coarse alignment" in some implementations. The augmented reality device may use its own camera(s) to detect the real world patient reference object from the viewpoint of the wearer and may attempt to detect the fiducials on the real world object. The augmented reality device may then determine the error or mismatch between the viewed location of the fiducials and the rendered location of the fiducials on the virtual object to determine the degree of accuracy in alignment and to adjust the location of the virtual object in the augmented reality coordinate system to better align it with the optically detected location of the real world patient reference object. In some cases the error in location of a virtual fiducial versus a real world fiducial optically detected by the augmented reality device camera(s) may be expressed as a displacement vector, x, y, z error values, or in other terms. The adjustments may be carried out in an iterative process to produce a best fit, for example using minimization of an optimization expression to bring the mismatch to within an overall threshold.

Whether manipulation of the virtual object is manual, automatic, or both manual and automatic, the alignment of the virtual object with the real world object may be signaled to the user by the augmented reality device. For example, if the augmented reality device determines the degree of mismatch between its optical view of the real world object and the rendered position of the virtual object, then it may determine the degree of alignment. For example, it may calculate the overall displacement between the location of the real world fiducials and each corresponding virtual fiducial to determine the degree of mismatch in alignment. It will be appreciated that a variety of calculations may be used to determine the degree of error in alignment. Once the virtual object is aligned with the real world object to within less than a maximum error, then the augmented reality device may signal success to the user by, for example, displaying the virtual object in a different colour (e.g. green), rendering a message or signal on the display, outputting an audio signal, or otherwise indicating successful alignment.

In some cases, the determination of alignment may be manual. That is, the user may signal to the device when the user sees the virtual object as aligned with the real world object. This may be signaled through any input mechanism, including gestures, voice recognition, hand-held input devices, or the like.

Once alignment occurs, the position of the fiducials tracked by the navigation system in the navigation coordinate system at that time and the position of the corresponding fiducials on the virtual object in the augmented reality coordinate system determine the transform between the two coordinate systems. The calculation of the transform may be carried out by the augmented reality device in some embodiments. In this respect, the navigation system may regularly transmit the location of the tracked fiducials in the navigation coordinate system to the augmented reality device over a communications link (e.g. wired or wireless or both), so that the augmented reality device has the most recent navigation system coordinates available when alignment occurs. The regular transmission of coordinates may be in response to the augmented reality device sending the navigation system a request based on initiation of the registration process. In some embodiments, the augmented reality device may request the coordinates once alignment is detected, and the navigation system then sends the current coordinates in response. In some embodiments, the navigation system may determine the transform based on the augmented reality system sending the navigation system the augmented reality coordinate system coordinates for the virtual object and an indication that alignment has occurred. The navigation system then determines the transform and provides the augmented reality device with details of the transform.

In some implementations, the registration process for the augmented reality system may include iterative refinements through repositioning of the augmented reality device. That is, once an alignment occurs, the augmented reality device may prompt a wearer to move his or her position to view the object from a different viewpoint. The wearer and/or the augmented reality device may then determine whether the alignment of the virtual model and the real world object remains aligned from the new viewpoint. The position of the virtual model may then be manually or automatically adjusted to improve the alignment. A change in viewpoint may then be prompted again to verify that the new position better maintains alignment. This process may be carried out until the alignment meets a minimum threshold of accuracy as the viewpoint changes, in some cases.

Figure 9:
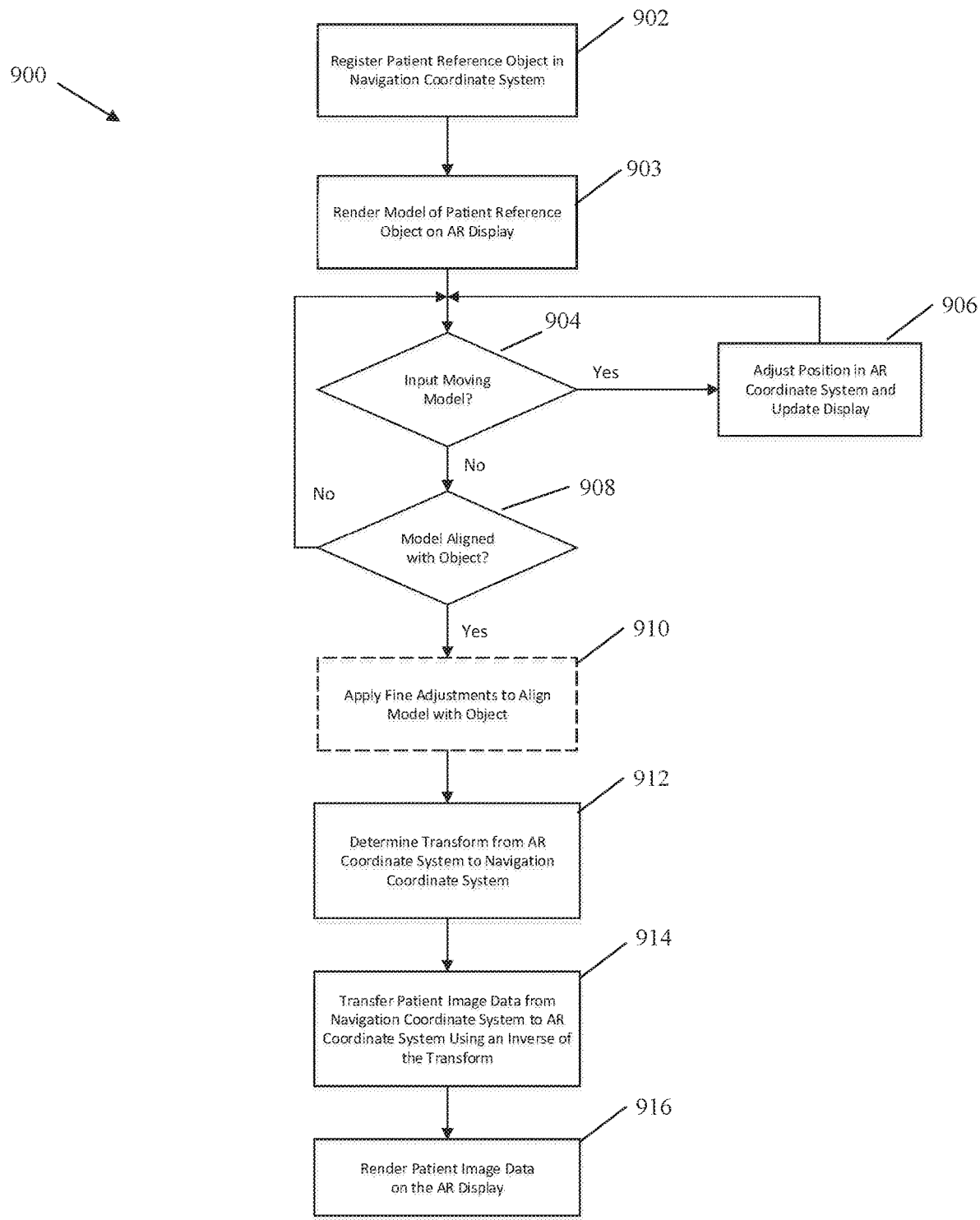
FIG. 9 shows, in flowchart form, an example registration process for an augmented reality device for use in a surgical procedure.

Reference is now made to FIG. 9, which shows, in flowchart form, one example registration process 900 for an augmented reality device for use in a surgical procedure. The process 900 is used in connection with an augmented reality device and a navigation system for optically-guided surgery.

As indicated by operation 902, the navigation system undergoes its own registration process for determining the location of the patient in the navigation coordinate system. The patient, in this example, is positioned in fixed relation to a trackable patient reference object. The registration process for the navigation system includes determining the positions of both the patient reference object and touch points or other features of the patient, so that the patient's location relative to the patient reference object is known. Thereafter, the navigation system tracks the location of the patient reference object, and is thereby able to track the location of the patient. Accordingly, operation 902 includes determining (and tracking) the location of the patient reference object in the navigation coordinate system.

In operation 903, the augmented reality device positions a virtual model of the patient reference object in the augmented reality coordinate system and renders the virtual model on the augmented reality device's display in accordance with its position in the augmented reality coordinate system. As indicated by operations 904 and 906, the augmented reality device then awaits input regarding changes to the position of the virtual model in the augmented reality coordinate system. As discussed above, the input may be provided via an input device, voice commands, or gesture commands, in some embodiments. For example, in one implementation, the wearer may be able to virtually "grasp" the virtual model with a particular gesture and move, rotate or otherwise manipulate the virtual model's position and orientation using other gestures detectable by the augmented reality device. Those adjustments to the position of the virtual model are made to the virtual model's orientation and position in the augmented reality coordinate system, which results in updated rendering of the virtual model rendered on the display.

In operation 908, the augmented reality device determines whether the virtual model of the patient reference object is aligned with the real world patient reference object. The determination may be based on a user input manually instructing the device that the alignment has occurred in some cases. In some embodiments, the determination may be made by the augmented reality device based on detecting the alignment. For example, the detection may be based on optically recognizing the fiducial markers or other features of the patient reference object and determining whether the rendered virtual model is sufficiently aligned with the real world device to meet a minimum threshold accuracy. In this example process 900, the described adjustments to the position of the virtual model are caused via user input. Optionally, as indicated in operation 910, the adjustments may be made automatically by the augmented reality device without user input. In some cases, the latter adjustments may be considered "fine" adjustments to refine the "coarse" positioning by the user. Operation 910 is described in greater detail in connection with FIG. 10, below.

Alignment of the virtual patient reference object with the real world patient reference object causes the augmented reality device (or navigation system in some other embodiments) to determine the transform between the navigation coordinate system and the augmented reality coordinate system, as indicated by operation 912. The relative locations of the fiducials on the patient reference object and the corresponding fiducials on the virtual model of the patient reference object in the navigation coordinates system and augmented reality coordinate system, respectively, at the time of alignment determine the transform between the two spaces.

In this example, in operation 914 patient image data that has been transformed to the navigation coordinate system is transferred to the augmented reality coordinate system based on the transform determined in operation 912. This places the image data in the augmented reality coordinate system, meaning the augmented reality device is then able to render the patient image data on the augmented reality display, as shown by operation 916. This may, for example, include rendering MRI or CAT scan data so that a wearer viewing the real world patient will see the pre-operative scanned image data positioned in alignment with the real world patient.

Figure 10:
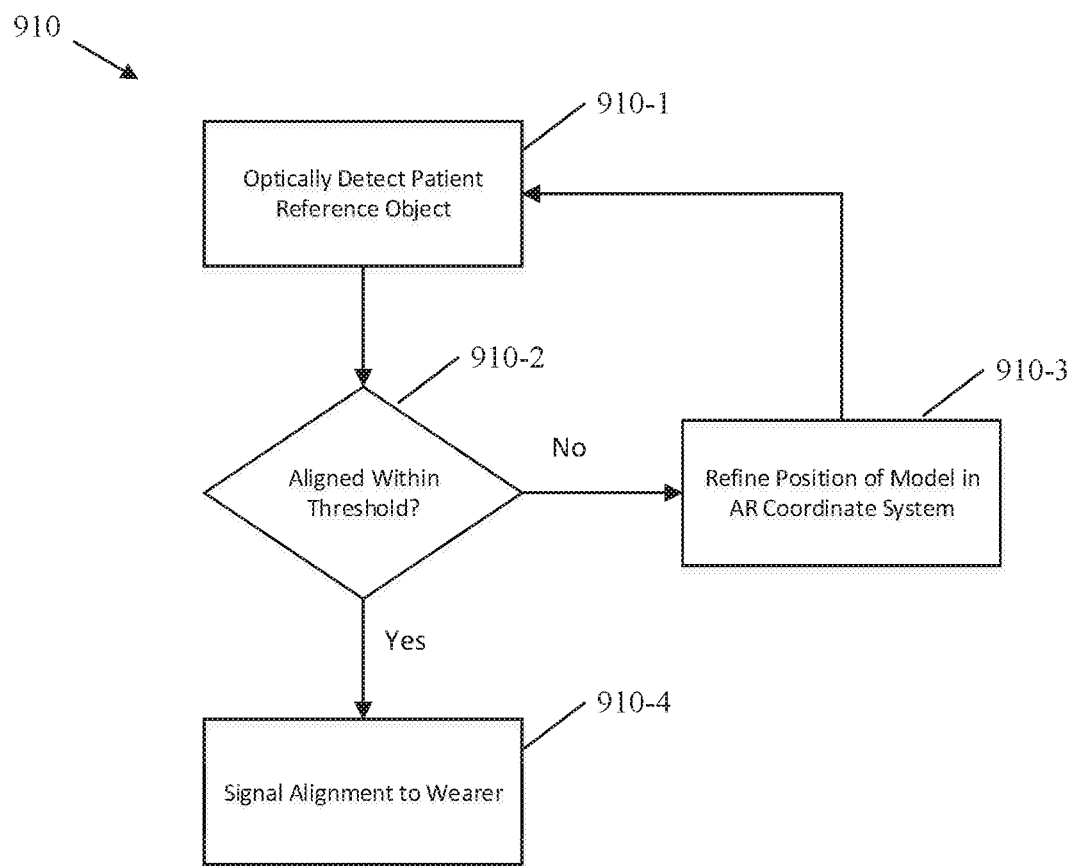
FIG. 10 shows, in flowchart form, an example process of refining the alignment by the augmented reality device.

FIG. 10 shows the optional process of refining the alignment by the augmented reality device. In operation 910-1, the augmented reality device optically detects the patient reference object using one or more cameras. The one or more cameras capture images of the real world objects in the wearer's field of view. Using object recognition or other techniques, the augmented reality device optically recognizes the patient reference object and/or the fiducials on the patient reference object. The augmented reality device may apply a slight transformation to the image data to bring it into the augmented reality coordinate system, having regard to the slight mismatch in the view point of the wearer and the position and orientation of the camera.

Having identified the patient reference object and/or its fiducial markers, the augmented reality device then determines the degree of mismatch between the optically detected location of the real world patient reference object and the position of the virtual model as defined in the augmented reality coordinate system. As discussed above, various techniques may be used to calculate the error in alignment; however, the error in many cases may be measured as the magnitude of three-dimensional vector displacement between one or more defined points of the patient reference object and the corresponding points on the model. The error is compared to a threshold in operation 910-2 and, if the error is determined to be above the threshold, then in operation 910-3 the augmented reality device adjusts the position and/or orientation of the model. That is, the augmented reality device may apply a positional adjustment (e.g. translation, orientation, etc.) to the virtual model of the patient reference object in the augmented reality coordinate system to attempt to reduce the magnitude of the error.

Once the virtual model and real world patient reference object have been aligned within the threshold maximum error permitted, then in operation 910-4 the augmented reality device may, in some embodiments, signal the successful alignment to the wearer. As mentioned above, the signal may be visual, auditory, kinetic, etc. In some cases, the signal may include causing the virtual model to change colour, flash, or otherwise visually signal to the wearer that a successful alignment has occurred and the wearer may now proceed to use the augmented reality device in the surgical procedure.

Certain adaptations and modifications of the described embodiments can be made. Therefore, the above discussed embodiments are considered to be illustrative and not restrictive.

What is claimed is:

1. A method of using an augmented reality device in a surgical procedure that uses an optical navigation system that optically tracks a patient reference object to locate the patient reference object in a real-world space and determine its coordinates in a navigation coordinate system, wherein the augmented reality device has a display through which a wearer views the real-world space and on which the augmented reality device may render modeled objects, wherein the augmented reality device includes sensors for determining a position and orientation of the augmented reality device in the real-world space using an augmented reality coordinate system, the method comprising:

rendering, on the display, a virtual model of the patient reference object;

in response to receiving a first input to manipulate a location of the virtual model of the patient reference object in the augmented reality coordinate system, changing a position of the virtual model of the patient reference object in the augmented reality coordinate system;

determining that the virtual model of the patient reference object is brought into alignment with the patient reference object in the real-world space from a viewpoint of the wearer of the augmented reality device as a result of the first input;

in response to determining that the virtual model of the patient reference object is aligned with the patient reference object in the real-world space as a result of the first input, identifying a first transform from the navigation coordinate system to the augmented reality coordinate system, wherein identifying the first transform comprises:

obtaining navigation coordinates data for a current location of the patient reference object in the navigation coordinate system; and determining a transform for translating said current location in the navigation coordinate system to coordinates for the corresponding and aligned virtual model of the patient reference object in the augmented reality coordinate system;

subsequently transferring patient image data from the navigation coordinate system to the augmented reality coordinate system using the first transform; and displaying the patient image data on the display to augment a real-world view of a patient, wherein the determining step involves a user input to perform first alignment of the virtual model of the patient reference object to the patient reference object in the real-world space, and wherein the patient reference object is in a fixed location relative to the patient.

2. The method claimed in claim 1, wherein the patient reference object comprises a solid body having at least four trackable fiducials attached thereto.

3. The method claimed in claim 2, wherein the virtual model of the patient reference object includes virtual fiducials that correspond to the at least four trackable fiducials, and wherein the determination that the virtual model of the patient reference object is aligned comprises determining that each virtual fiducial is aligned with its corresponding trackable fiducial on the patient reference object.

4. The method claimed in claim 1, wherein receiving input further comprises receiving input via an input device specifying a change in position or orientation for the virtual model of the patient reference object within the augmented reality coordinate system.

5. The method claimed in claim 4, wherein the input comprises gesture-based input.

6. The method claimed in claim 1, wherein determining that the virtual model of the patient reference object is aligned comprises determining that an error in alignment between a position of the virtual model of the patient reference object and a position of the patient reference object is less than a threshold amount.

7. The method claimed in claim 6, wherein the error in alignment is based on a three-dimensional distance in the augmented reality coordinate system between at least one point on the virtual model of the patient reference object and a corresponding point on the patient reference object.

8. The method claimed in claim 7, wherein said at least one point comprises a virtual fiducial.

9. The method claimed in claim 1, wherein determining that the virtual model of the patient reference object is aligned comprises determining that the virtual model of the patient reference object is aligned with the patient reference object in the real-world space within a coarse error threshold, automatically adjusting a position of the virtual model to minimize an error in alignment, and determining that the virtual model of the patient reference object is aligned with the patient reference object in the real-world space within a fine error threshold that is smaller than the coarse error threshold.

10. The method claimed in claim 9, wherein automatically adjusting comprises determining a location of the patient reference object in the augmented reality coordinate system and applying a translation or rotation to the virtual model of the patient reference object to minimize the error in alignment of the virtual model of the patient reference object with the location of the patient reference object in the augmented reality coordinate system.

11. The method claimed in claim 10, wherein the augmented reality device further includes a camera, and wherein the determining a location of the patient reference object comprises capturing an image and detecting the location of the patient reference object using image recognition within the image.

12. The method claimed in claim 1, further comprising outputting a prompt to change a location of the augmented reality device to view the patient reference object from another angle.

13. A surgical navigation system to track objects during a surgical procedure, the surgical navigation system comprising:

an optical tracking system that optically tracks a patient reference object to locate the patient reference object in a real-world space and determine its coordinates in a navigation coordinate system; and an augmented reality device having a display through which a wearer views the real-world space and on which the augmented reality device may render modeled objects, and including sensors for determining a position and orientation of the augmented reality device in the real-world space using an augmented reality coordinate system, the augmented reality device to:

render a virtual model of the patient reference objection on the display;

receive a first input to manipulate a location of the virtual model of the patient reference object in the augmented reality coordinate system; and in response to receiving the first input, change a position of the virtual model of the patient reference object in the augmented reality coordinate system, wherein the augmented reality device is to determine that the virtual model of the patient reference object is brought into alignment with the patient reference object in the real-world space from a viewpoint of the wearer of the augmented reality device as a result of the first input;

wherein the optical tracking system or the augmented reality device is to, in response to determining that the virtual model of the patient reference object is aligned with the patient reference object in the real-world space as a result of the first input, identify a first transform from the navigation coordinate system to the augmented reality coordinate system, wherein identifying the first transform comprises:

obtaining navigation coordinates data for a current location of the patient reference object in the navigation coordinate system; and determining a transform for translating said current location in the navigation coordinate system to coordinates for the corresponding and aligned virtual model of the patient reference object in the augmented reality coordinate system; and wherein the optical tracking system or the augmented reality device is to subsequently transfer patient image data from the navigation coordinate system to the augmented reality coordinate system using the first transform, and wherein the augmented reality system is to display the patient image data on the display to augment a real-world view of a patient, wherein the determining step involves a user input to perform first alignment of the virtual model of the patient reference object to the patient reference object in the real-world space, and wherein the patient reference object is in a fixed location relative to the patient.

14. The surgical navigation system claimed in claim 13, wherein the patient reference object comprises a solid body having at least four trackable fiducials attached thereto.

15. The surgical navigation system claimed in claim 14, wherein the virtual model of the patient reference object includes virtual fiducials that correspond to the at least four trackable fiducials, and wherein the determination that the virtual model of the patient reference object is aligned comprises determining that each virtual fiducials is aligned with its corresponding trackable fiducial on the patient reference object.

16. The surgical navigation system claimed in claim 13, wherein the augmented reality device further comprises an input device to receive input specifying a change in position or orientation for the virtual model of the patient reference object within the augmented reality coordinate system.

17. The surgical navigation system claimed in claim 13, wherein the augmented reality device is to determine that the virtual model of the patient reference object is aligned by determining that an error in alignment between a position of the virtual model of the patient reference object and a position of the patient reference object is less than a threshold amount.

18. The surgical navigation system claimed in claim 17, wherein the error in alignment is based on a three-dimensional distance in the augmented reality coordinate system between at least one point on the virtual model of the patient reference object and a corresponding point on the patient reference object.

19. The surgical navigation system claimed in claim 13, wherein the augmented reality device is to determine that the virtual model of the patient reference object is aligned by determining that the virtual model of the patient reference object is aligned with the patient reference object in the real-world space within a coarse error threshold, automatically adjust a position of the virtual model of the patient reference object to minimize an error in alignment, and determine that the virtual model of the patient reference object is aligned with the patient reference object within a fine error threshold that is smaller than the coarse error threshold.

20. The surgical navigation system claimed in claim 19, wherein the augmented reality device is to automatically adjust by determining a location of the patient reference object in the augmented reality coordinate system and applying a translation or rotation to the virtual model of the patient reference object to minimize the error in alignment of the virtual model of the patient reference object with the location of the patient reference object in the augmented reality coordinate system.

21. The surgical navigation system claimed in claim 20, wherein the augmented reality device further includes a camera, and wherein the augmented reality device is to determine a location of the patient reference object by capturing an image and detecting the location of the patient reference object using image recognition within the image.

* * * * *